(12) United States Patent
Quelle et al.

(10) Patent No.: US 7,442,389 B2
(45) Date of Patent: Oct. 28, 2008

(54) METHODS OF ADMINISTERING MICROPARTICLES COMBINED WITH AUTOLOGOUS BODY COMPONENTS

(75) Inventors: Gerhard Quelle, Wald-Michelbach (DE); Russell J. Anderson, San Diego, CA (US); Stefan M. Lemperle, San Diego, CA (US)

(73) Assignee: Artes Medical, Inc., San Diego, CA (US)

( * ) Notice: Subject to any disclaimer, the term of this patent is extended or adjusted under 35 U.S.C. 154(b) by 0 days.

(21) Appl. No.: 11/210,273

(22) Filed: Aug. 22, 2005

(65) Prior Publication Data

US 2006/0093644 A1 May 4, 2006

Related U.S. Application Data

(60) Provisional application No. 60/603,445, filed on Aug. 20, 2004.

(51) Int. Cl.
*A61K 9/14* (2006.01)
*A61F 2/00* (2006.01)

(52) U.S. Cl. .................... 424/489; 424/423

(58) Field of Classification Search ................ 424/423, 424/486, 489, 497
See application file for complete search history.

(56) References Cited

U.S. PATENT DOCUMENTS

| | | | | |
|---|---|---|---|---|
| 4,645,503 A | * | 2/1987 | Lin et al. ................ | 623/23.58 |
| 4,913,903 A | * | 4/1990 | Sudmann et al. ............ | 424/426 |
| 4,994,084 A | * | 2/1991 | Brennan ...................... | 128/898 |
| 5,356,629 A | * | 10/1994 | Sander et al. ............... | 424/422 |
| 5,922,025 A | * | 7/1999 | Hubbard ..................... | 424/423 |
| 6,323,278 B2 | | 11/2001 | Rhee et al. | |
| 6,336,028 B1 | * | 1/2002 | Vogel et al. ................ | 424/422 |
| 6,432,437 B1 | * | 8/2002 | Hubbard ..................... | 424/424 |
| 6,458,889 B1 | | 10/2002 | Trollsas et al. | |
| 6,533,819 B1 | | 3/2003 | Urry et al. | |
| 6,685,963 B1 | * | 2/2004 | Taupin et al. ............... | 424/486 |
| 6,699,294 B2 | | 3/2004 | Urry | |
| 6,969,400 B2 | | 11/2005 | Rhee et al. | |
| 2002/0025340 A1 | * | 2/2002 | Dyer .......................... | 424/486 |
| 2002/0094959 A1 | * | 7/2002 | DesRosiers .................. | 514/21 |
| 2002/0176893 A1 | * | 11/2002 | Wironen et al. ............. | 424/489 |
| 2003/0171451 A1 | * | 9/2003 | White et al. ................ | 523/117 |
| 2004/0058008 A1 | * | 3/2004 | Tarcha et al. ............... | 424/490 |
| 2004/0091540 A1 | * | 5/2004 | Desrosiers et al. .......... | 424/486 |
| 2005/0027070 A1 | | 2/2005 | Rhee et al. | |
| 2006/0058890 A1 | * | 3/2006 | Lesh ....................... | 623/23.72 |

OTHER PUBLICATIONS

Lemperle et al., Artecoll product description sheet, 1 page, downloaded from www.artecoll.com/description.htm, ca. 1993.*
International Search Report and The Written Opinion of the International Searching Authority, or the Declaration for PCT/US05/29672 dated Sep. 25, 2006.

* cited by examiner

*Primary Examiner*—Sharon E. Kennedy
(74) *Attorney, Agent, or Firm*—Heller Ehrman LLP

(57) ABSTRACT

Microspheres to be implanted into a patient are metered and mixed with fluids, cells, or tissues withdrawn from the patient's own body, and reinserted into the patient's body to achieve augmentation, repair or other treatment of the patient's tissue.

41 Claims, 2 Drawing Sheets

METHODS OF ADMINISTERING MICROPARTICLES COMBINED WITH AUTOLOGOUS BODY COMPONENTS

CROSS-REFERENCE TO RELATED APPLICATIONS

This application claims the benefit of U.S. Provisional Application No. 60/603,445, filed Aug. 20, 2004 and entitled USE OF AUTOLOGOUS BODY FLUIDS AND TISSUES COMBINED WITH MICROSPHERES, the entire contents of which are expressly incorporated herein by reference.

BACKGROUND OF THE INVENTION

1. Field of the Invention

This invention relates to medical implants and, more particularly, to the metering and mixing of microspheres with fluids and other components for insertion into the patient's body to achieve augmentation or repair of tissues.

2. Description of Related Art

Microspheres and microparticles, such as described in U.S. Pat. No. 5,344,452, the entire contents of which are incorporated herein by reference, made of for example polymethylmethacrylate (PMMA) or other materials, are currently combined with foreign carrier materials (e.g., bovine collagen) and injected or introduced into the body to accomplish augmentation or repair of various tissues.

The use of foreign materials as carriers for such microspheres may in some instances subject a patient to immune reactions, risks of infection, or introduction of viral agents. Complications can result which may range from mild local irritation to serious and potentially fatal introductions of viruses from the foreign carrier material.

A need exists in the prior art for carrier materials capable of presenting reduced risks to the patient in the context of introducing microspheres and microparticles into patient tissues for augmentation or repair of the tissues.

SUMMARY OF THE INVENTION

The present invention addresses this need by providing autologous carrier materials for use with microparticles in tissue augmentation and repair procedures implemented on a patient. Use of the patient's own autologous tissues, cells, or fluids as the carrier material for microparticles can reduce the likelihood of viral infection and eliminate adverse reactions from the patient's body to foreign carrier materials.

In accordance with certain aspects of the present invention, objects and advantages of the methods and features described herein may include one or more of the following: a) providing a biocompatible augmentation or repair material that is free from viral contaminants which can be present in foreign carrier materials; b) providing a biocompatible augmentation or repair material that is more readily accepted by the patient's body, as a result of the augmentation or repair material carrier material being harvested from the host patient and later reintroduced; c) providing a biocompatible augmentation or repair material that can be produced with relative ease using, for example, a sterile aspiration syringe to perform one or more of withdrawal of autologous tissues, cells, or fluids, mixing of the autologous tissues, cells, or fluids with a predetermined amount of microparticles, and reintroduction of the autologous tissues, cells, or fluids with microparticles back into the patient's body; and d) to provide a biocompatible augmentation or repair material which can contain other desirable materials, such as but not limited to one or more of an agent to assist in homogeneity, a coagulant agent, an agent to facilitate bonding, an agent for facilitating gelation, an adhesion prevention agent, an antibiotic agent, an anesthetic agent, an anti-inflammatory agent, and other materials which may be capable of for example being introduced into a sterile aspiration syringe and mixed (e.g., gelatinized) with the patient's own fluids, cells, or tissue to achieve a suitable or optimal approach to or correction of an issue or problem, and combinations including one or more of the preceding items. The microparticles can comprise microspheres, and the sterile aspiration syringe can comprise a metered aspiration, mixing, and delivery system.

While apparatuses and methods of the present invention have or will be described for the sake of grammatical fluidity with functional explanations, it is to be expressly understood that the claims, unless expressly formulated under 35 U.S.C. 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. 112 are to be accorded full statutory equivalents under 35 U.S.C. 112.

Any feature or combination of features described herein are included within the scope of the present invention provided that the features included in any such combination are not mutually inconsistent as will be apparent from the context, this specification, and the knowledge of one skilled in the art. In addition, any feature or combination of features may be specifically excluded from any embodiment of the present invention. For purposes of summarizing the present invention, certain aspects, advantages and novel features of the present invention are described herein. Of course, it is to be understood that not necessarily all such aspects, advantages or features will be embodied in any particular embodiment of the present invention. Additional advantages and aspects of the present invention are apparent in the following detailed description and claims that follow.

DETAILED DESCRIPTION OF THE INVENTION

Figure 1:
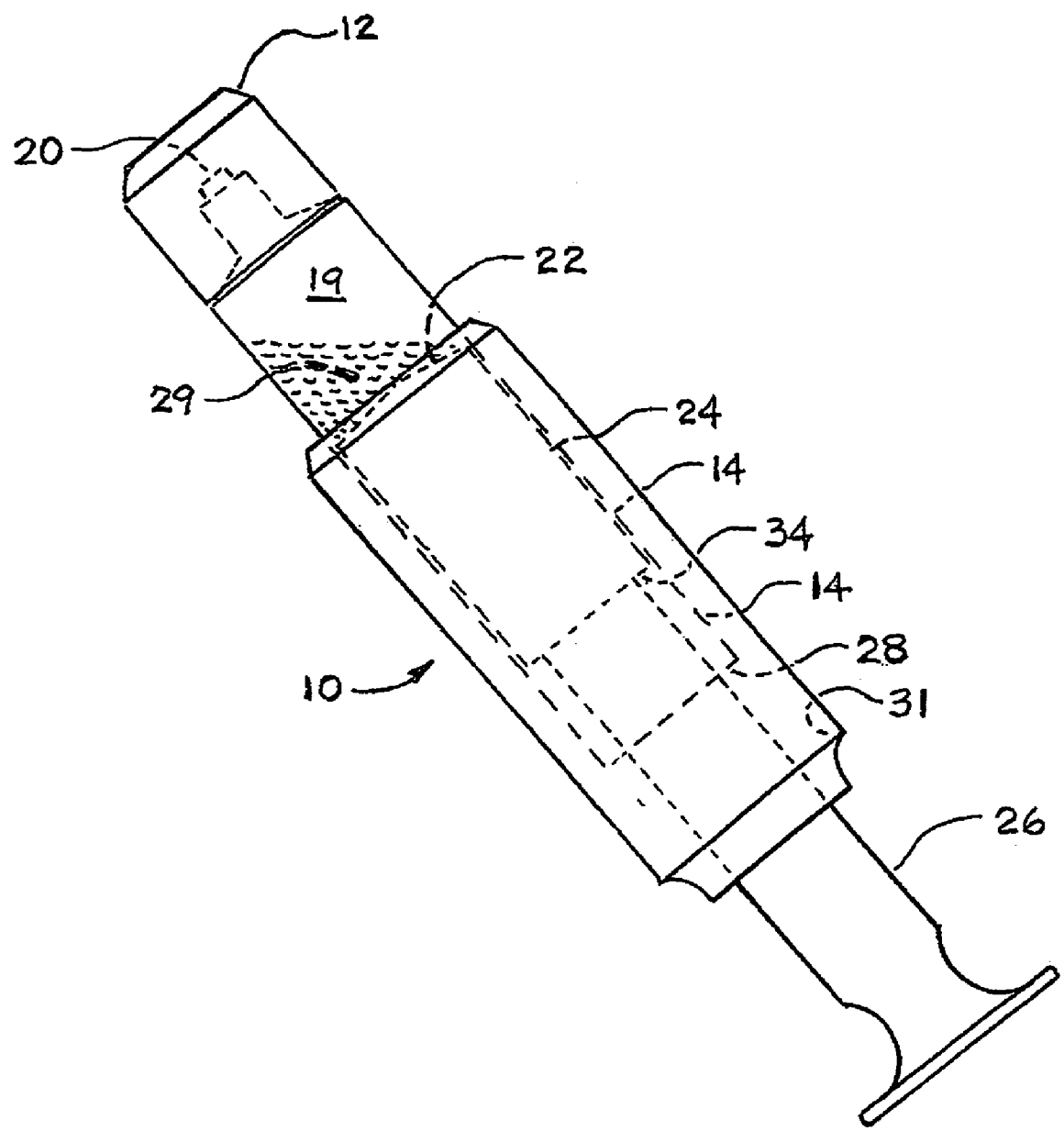
FIG. 1 is a pictorial diagram of a metered aspiration, mixing, and delivery system according to an exemplary implementation of the present invention.

Reference will now be made in detail to the presently preferred embodiments of the invention, examples of which are illustrated in the accompanying drawings. Wherever possible, the same or similar reference numbers may be used in the drawings and the description to refer to the same or like parts. It should be noted that the drawings are in simplified form and are not to precise scale. In reference to the disclosure herein, for purposes of convenience and clarity only, directional terms, such as, top, bottom, left, right, up, down, upper, lower, over, above, below, beneath, rear, and front, may be used. Such directional terms should not be construed to limit the scope of the invention in any manner.

Although the disclosure herein refers to certain illustrated embodiments, it is to be understood that embodiments presented herein are by way of example and not by way of limitation. The intent of this disclosure, while discussing exemplary embodiments, is that the following detailed description be construed to cover all modifications, alternatives, and equivalents of the embodiments as may fall within the spirit and scope of the invention as defined by the appended claims. It is to be understood and appreciated that the process steps and structures described herein do not cover a complete process flow for operations involving tissue augmentation and repair. The present invention may be practiced in conjunction with various techniques that are conventionally used in the art, and only so much of the commonly practiced process steps are included herein as are necessary to provide an understanding of the present invention.

The methods and systems described herein can allow physicians to repair, treat or augment a patient's tissue using a tissue treatment implant which may take the form of a biocompatible augmentation or repair material. The tissue treatment implant can comprise microparticles and a biocompatible medium in the form of an autologous carrier material. The autologous carrier material can be formed, at least in part, from an autologous component (e.g., tissue, cells, or fluid) removed or derived, at least in part, from the host patient's own body. The autologous carrier material may comprise a liquid or gel and, in addition to at least one autologous component (e.g., tissue, cells, or fluid), may comprise, for example, one or more of water and saline. In certain implementations, the autologous carrier material can comprise one or more of a collagen and a gelatin, which may or may not comprise the autologous component or components, and which may be degradable in a mammalian body. In certain instances, the autologous carrier may comprise, or may include as a main constituent, for example, one or more of a collagen, a component of collagen, gelatin, hydrolyzed collagen, hydrolyzed gelatin, fractions of hydrolyzed gelatin, elastin, a component of elastin, cerebral spinal fluid, and combinations thereof, any one or more of which may be autologous in accordance with one aspect of the present invention or non-autologous in accordance with another aspect of the present invention. In some instances, the autologous carrier may comprise, for example, one or more of connective tissue, adipose tissue, subcutaneous fat, loose or flaccid body fat, fat around the patient's waistline, cellulite, marrow, fibrous tissue, muscle tissue, cartilage tissue such as ear, ribs, or knee cartilage tissue, dermal tissue, mucosa, cells or stem cells, blood, blood serum, blood plasma, blood platelets, blood thrombin, blood fibrinogen or fibrin, cerebral spinal fluid, lymph, synovia, extracellular fluid, amniotic fluid, milk, cells which are native to or derived from a bodily fluid, components thereof, and combinations thereof, in any ratio, any one or more of which may be autologous in accordance with one aspect of the present invention or non-autologous in accordance with another aspect of the present invention. According to implementations wherein the autologous carrier comprises, for example, an autologous bodily fluid, the bodily fluid may be filtered through a sterile 0.2 micron filter before mixing with microparticles to remove microorganisms.

The biocompatible medium may comprise one or more of sterile water; an aqueous isotonic solution of saline; an aqueous isotonic solution of phosphate salts; a hypertonic aqueous solution; a hypotonic solution; a sterile aqueous thickening agent including one or more of collagen, gelatin, hyaluronic acid, methyl-cellulose, and polylactic acid; a component thereof, and combinations thereof. Furthermore, or alternatively, the biocompatible medium can be admixed with, for example, a tenside or other agent that changes the surface tension of a given fluid (e.g., water) so that the microparticles, and in particular embodiments, the polymer microparticles, float or are suspended better. The microparticles can in one implementation comprise a histocompatible solid in the form of a powder. The microparticles forming the histocompatible solid may be incorporated into the autologous carrier material and injected, for instance, with an injection needle at a desired treatment region.

The methods and implants of the present invention can attenuate or eliminate the introduction of viruses and other undesirable foreign matter into the patient's tissue, since in accordance with typical implementations the use of foreign carriers is attenuated or eliminated. The patient's body commonly will not reject the autologous carrier material to the extent it is harvested or derived at least in part from the patient rather than from another organism. The systems and methods described herein can involve utilization of a sterile aspiration syringe, which in a representative embodiment may comprise a metered aspiration, mixing, and delivery system. Such metered aspiration, mixing, and delivery systems can, in accordance with an aspect of the present invention, significantly enhance the safety and efficacy of particular implementations of combining microparticles (e.g., microspheres such as alloplastic and/or sterile microspheres) with autologous tissues, cells, or fluids for implantation into the patient. The autologous carrier materials of the present invention can further be mixed or combined with any one or more of a plethora of sterile or sterilizable materials and gelating agents to achieve any one or more of a broad range of desired properties such as, or in addition to, those of facilitating augmentation and repair as described herein.

As for composition, the microparticles in accordance with certain implementations of the present invention can comprise a cured polymer, such as a polymethacrylate or a polymethylmethacrylate (PMMA). In one implementation, the microparticles can comprise solid microparticles, which may take the form in one embodiment of non-porous beads. In modified implementations, the microparticles may not be altogether solid, such as implementations involving hollow or porous microparticles.

The microparticles can have a short-term effectiveness of up to about 6 months, a medium-term effectiveness of up to about 3 years, and/or a long-term effectiveness of more than about 3 years. The microparticles can be made at least in part of biological materials, such as, for example, but not limited to, one or more of any type of collagen, hyaluronic acid (e.g., animal derived, human derived and/or tissue/cell culture derived), genetically altered cells, tissues, organisms, genetically altered or not (e.g., purified cytoskeleton of unicellular and/or multicellular algae and/or other organisms), whether cross-linked or not cross-linked, or made of a synthetic and/or polymeric material, such as, for example, polylactic acid, organic compounds, inorganic compounds, ceramic materials, polymethacrylate, PMMA, polypropylene, polytetrafluoroethylene (PTFE), and combinations thereof.

As used herein, the term "microparticles" refers to microparticles (e.g., in a dust or powder form) possessing a diameter of at least about 10 microns. Typically, the average diameter will be greater than about 15 microns rendering the microparticles too large to be "eaten" by monocytes. The microparticles can have diameters sufficient to keep them from being washed away through lymph tracts or other tissue tracts from the implantation site. If the microparticles do not have a spherical form, then the diameter as used herein may refer to the greatest diameter of the smallest cross sectional area. It is, however, also possible to use different sized (e.g., smaller) microparticles. Typically, the microparticles will have an average diameter less than about 200 microns. In representative embodiments, the microparticles can have an average diameter of about 15 to about 200 microns and in certain implementations from about 15 to about 60 microns. It may be possible in modified embodiments for diameters to range from about 10 microns to about 500 microns. In certain configurations, the microparticles are small enough to be injected through a fine gauge cannula or an injection syringe to the desired treatment region. Microparticles having the diameters specified herein may have a relatively minimal effect on surrounding tissues.

The microparticles used according to exemplary embodiments of the present invention have smooth or non-turbulent surfaces that are, for example, free from one or more of corners and edges. In similar implementations, the microparticles of these embodiments may be formed at least in part not to have sharp transitions on their surfaces, wherein transitions are for instance found at such corners and edges. In addition, they may be formed not to have peaks of any kind or tapered projections. Consequently, transitions from one outer surface to the other outer surface of one or more of the microparticles as used according to these embodiments of present invention can occur in a continuous manner. If such transitions are present, as is the case for the edges of a cube, such transitions can be smoothed or rounded. Due to the smooth surfaces of the above-described types of microparticles, damage or irritation to cells and other tissue structures can be altered, minimized, or avoided. In addition, according to an aspect of the present invention, the danger of causing reactions of the tissue, such as foreign body reactions or granulous formation in response to sharp edges, which may be followed by infections, can be altered, attenuated, or eliminated.

In addition to spherical forms, the microparticles may comprise, as a few examples, one or more of elliptical (e.g., extruded, molded and/or machined) or cylindrical (e.g., extruded, molded and/or machined) forms, and further may comprise, for example, one or more of smoothed or rounded corners, edges, peaks, and projections. Other implementations may not include smoothed or rounded corners, edges, peaks, and projections.

According to exemplary embodiments of the present invention, microparticles which are crystalline (for instance needle-shaped) or microparticles which have been obtained by mechanically breaking up greater units into smaller pieces, may not be used, in some embodiments, to the extent the microparticles possess the above-mentioned sharp edges and corners. In modified embodiments, these types of microparticles may be used in whole or in part, such as, for example, embodiments comprising microparticles possessing one or more of sizes between about 10 microns and about 500 microns, an absence of smooth surfaces, an absence of corners, edges, peaks, or projections, and an absence of smooth or rounded corners, edges, peaks, and projections.

The microparticles may comprise one or more of a solid body, a porous surface (e.g., a surface impregnated with a material that is subsequently dissolved out), a porous body (e.g., formed by coating an expandable material and then heating, so that the expandable material inside forms a gas and expands forming channels to the surface), a hollow interior (e.g., formed by providing a feed tube into a center of a die for forming a microparticle, whereby as material is passed into the die for molding gas is injected into a central area of the material within the die), a shell-like structure (e.g., formed by coating and/or dissolving-out an interior beneath the coating), a metallic coating, a carbon coating, a carbon nanotube coating, a non-coated surface, components thereof, and combinations thereof in any ratio. According to certain implementations, surfaces of the microparticles of the present invention do not have pores. In other implementations of the present invention, however, parts or all of the surfaces of the microparticles may comprise pores. In certain implementations, dynamically balanced microparticles and in particular instances microparticles having elliptic or spherical forms can be used. In some examples, it is possible to use microparticles of a different geometrical form, and, when in the context of smooth-surfaced implementations, all or a majority of the microparticles may have smooth or smoothed-off surfaces.

When formed with smooth surfaces and the disclosed sizes, the microparticles used may not be detected by the endogenous macrophages as foreign bodies so that no or reduced defensive reactions take place. According to a representative embodiment, the microparticles have spherical forms or sphere-like forms capable of forming closely-packed arrangements at the site where they have been implanted and further capable of being individually encapsulated by scar tissue of the host. For instance, the microparticles, which in a representative embodiment may comprise PMMA spherical beads, after being inserted into the treatment region, may be encapsulated by delicate capsules of connective tissue and/or embedded into connective tissue or fibers where they remain stationary in the tissue.

According to exemplary implementations, regarding maturation of the microparticles, which in a representative embodiment may comprise PMMA spherical beads, as a result of the size and physical stability of the PMMA beads, they cannot be phagocytised or lysed. In order to isolate the foreign body, the animal body can only fibrotically wall off the foreign bodies in the form of scar tissue. Such a process typically takes place with almost any foreign body which cannot be destroyed by the animal body.

To the extent present, the fibrotic growth of connective tissue can be a natural reaction to one or more of the lesion of the tissue caused by the injection cannula (e.g., needle) and the presence of the microparticles. The fibrotic reaction may occur, for example, during 3 to 6 months after injection of the biocompatable augmentation or repair material due, for example, to the smooth and chemically inert surfaces of the microparticles (e.g., PMMA beads). From then on, the beads can remain in the tissue without reaction and provide for the formation and existence of permanent fibrovascular connective tissue.

The microparticles used, according to representative implementations of the present invention, can comprise a polymer, and in particular a completely cured and fully polymerised polymer so that no remaining monomers, which may be toxic or may cause cancer, are incorporated into the body of the treated patient. In principle, it is possible to use any inert histocompatible polymer for producing the microparticles used according to the present invention. Modified embodiments may comprise, in whole or in part, non-polymer microparticles. In an exemplary embodiment, the biocompatable alloplastic implant comprises one or more of the implants described under the name Artecoll® and obtainable at www.artecoll.com or www.canderm.com, or ArteFill® and obtainable at www.artefill.com.

Figure 2:
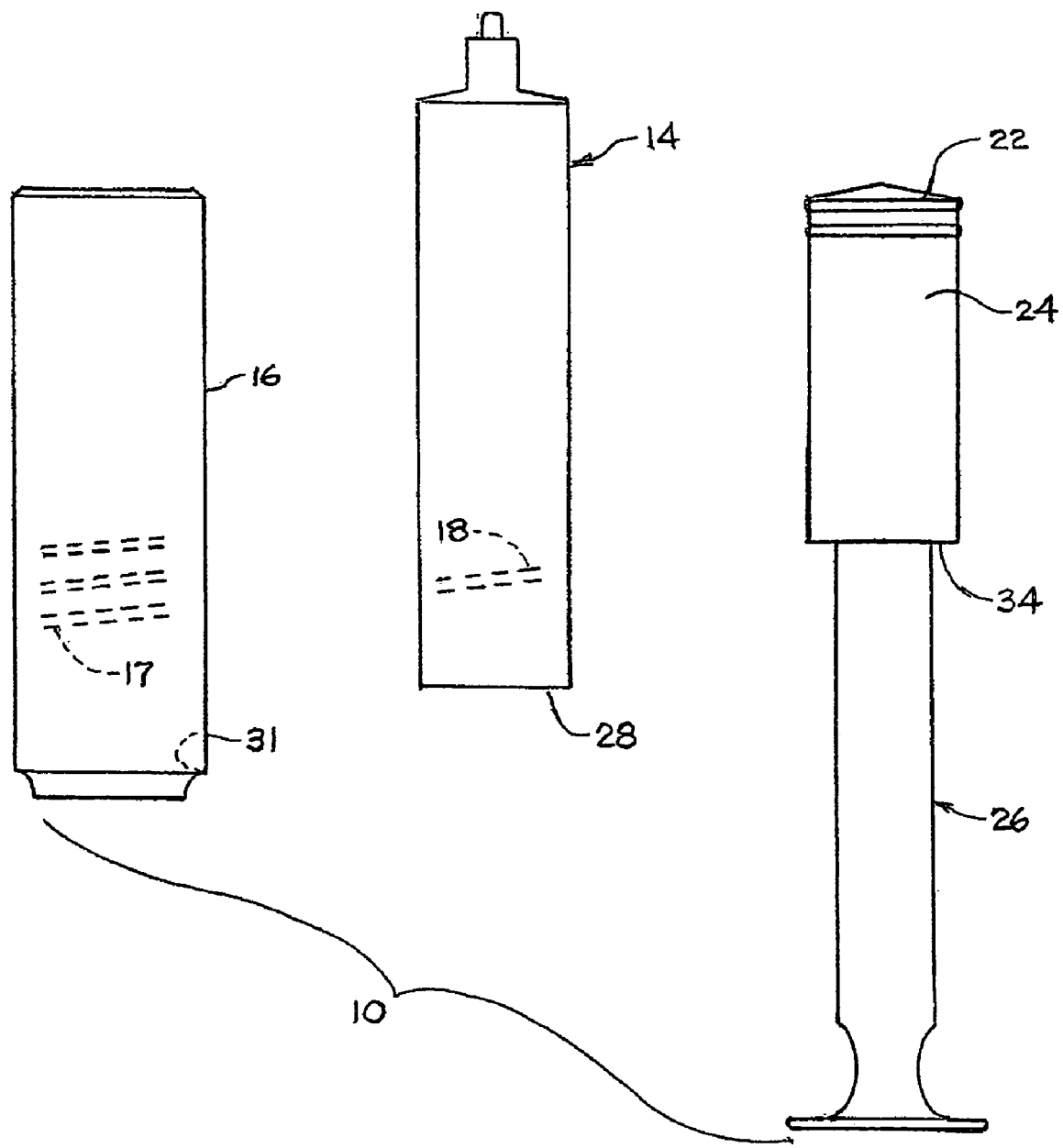
FIG. 2 is an exploded diagram showing individual element that operate together to form the metered aspiration, mixing, and delivery system of FIG. 1.

Referring more particularly to the drawings, one typical embodiment of this invention can be described by referring to a metered aspiration, mixing, and delivery system 10 as shown in FIGS. 1 and 2. A pictorial representation of the metered aspiration, mixing, and delivery system 10 according to an exemplary implementation of the present invention is provided in FIG. 1, and an exploded diagram showing individual elements that operate together to form the metered aspiration, mixing, and delivery system 10 of FIG. 1 is provided in FIG. 2. The sterile barrier system closure or threaded cap 12 is removed from the metered aspiration, mixing, and delivery system 10 and replaced with a sterile needle or cannula (not shown). The needle or cannula is then inserted into the patient, and the desired body autologous component (e.g., tissue, cells, or fluid) or components can be withdrawn by aspiration into a system barrel 14. In modified embodiments, the needle or cannula can be inserted into other autologous component sources (e.g., autologous tissue, cells, fluid, or other sources), and the desired autologous tissue, cells, or fluid withdrawn or otherwise collected into the system barrel 14.

As presently embodied, the system barrel 14 can be metered to control the amount of fluid or material to be aspirated or otherwise collected, if desired. In the illustrated embodiment, a rotatable metering sleeve 16 provides for metering or adjustment of the size of a usable volume 19, which can be defined as a part of the system barrel 14 that is available for use. As presently embodied, the usable volume 19 is defined as a volume in the distal end of the system barrel 14 that is bordered by a distal end 22 of a plunger cylinder 24, which is movable distally and proximally by the hand of a user. The plunger cylinder 24 may be connected, for example, to a plunger rod 26. Thus, the distal end 22 of the plunger cylinder 24 can be inserted into a proximal end 28, and the distal end 22 can be advanced distally and retracted proximally to decrease and increase the size of the usable volume 19, respectively.

According to a typical use, autologous and/or other components may be introduced into the usable volume 19 by way of ingress through, for example, the luer connection 20. Additionally, autologous and/or other components may be introduced into the usable volume 19 by way of ingress through, for example, the proximal end 28 of the system barrel 14. In a typical implementation, a prefill media (e.g., comprising microparticles or microspheres) 29 may be introduced into the usable volume 19 through the luer connection 20, prior to insertion of a needle or cannula into a patient and withdrawal of a desired body autologous component (e.g., tissue, cells, or fluid) or components by aspiration into the usable volume 19 of the system barrel 14. Once a desired component has been aspirated into the usable volume 19 of the system barrel 14, it can be mixed with the prefill media (and, optionally further processed) for subsequent introduction (e.g., ejection out of the luer connection) into a patient. Generally, various types of processing may be implemented on components, autologous and/or otherwise, at various points in time and/or various locations. For example, the metered aspiration, mixing and delivery system 10 may be operated in conjunction with a micronizing function, which, for example, may be implemented with one or more of structure configured to perform physical micronization (e.g., by way of a rotating cutter disposed in the usable volume 19 of the system barrel 14) and structure configured to perform ultrasonic micronization (e.g., by way of application of ultrasonic energy from an external source to the usable volume 19 of the system barrel 14), a component of either, and combinations thereof. Additionally, or alternatively, any implementation of the metered aspiration, mixing and delivery system 10 described herein may be operated in conjunction with a filtering function, such as, for example, an implementation wherein autologous fluid (or, in modified embodiments, tissue, cells and/or fluid) is passed through a sterile filter (e.g., a 0.2 micron filter to remove microorganisms) formed within or in conjunction with a syringe or metered aspiration, mixing and delivery system, for example, before mixing with microparticles.

In the illustrated embodiment, rotation of the metering sleeve 16 in a first direction provides for an increase in the usable volume 19 of the system barrel 14, and rotation of the metering sleeve 16 in a second direction provides for a decrease in the usable volume 19 of the system barrel 14. As presently embodied, the metering sleeve 16 comprises threads (not shown) on an interior surface that engages corresponding threads (not shown) on an exterior surface of the system barrel 14, so that rotation of the metering sleeve 16 in clockwise and counter-clockwise directions advances the metering sleeve 16 in distal and proximal directions, respectively, with respect to the system barrel 14.

Movement of the distal end 22 of the plunger cylinder 24 in the proximal direction is always limited by a plunger cylinder stop 31, which is connected to and which is formed on an interior surface of the metering sleeve 16. That is, without the metering sleeve 16, the plunger cylinder 24 is free to move distally and proximally within the system barrel 14. Introduction of the metering sleeve 16, however, serves to limit proximal movement of the plunger cylinder 24, since the plunger cylinder stop 31 does not allow a proximal end 34 of the plunger cylinder 24 to pass proximally through the plunger cylinder stop 31.

When the metering sleeve 16 is attached to the barrel system 14 and moved to a full distal position, a proximal end 28 of the system barrel 14 is generally aligned with (e.g., abuts with) the plunger cylinder stop 31 so that the proximal end 34 of the plunger cylinder 24 can be moved proximally only as far as the plunger cylinder stop 31 of the metering sleeve 16. When the metering sleeve 16 is attached to the barrel system 14 and moved to a full proximal position, the plunger cylinder stop 31 at the proximal end of the metering sleeve 16 extends proximally beyond the proximal end 28 of the system barrel 14 so that the proximal end 34 of the plunger cylinder 24 can be moved proximally past the proximal end 28 of the system barrel 14 all the way back (in the proximal direction) to the proximal end of the metering sleeve 16 (to abut with the plunger cylinder stop 31).

The barrel can contain, for example, a prefill media 29 comprising, for example, microparticles (e.g., microspheres). Micropoarticles and/or any other materials (e.g., sterile materials) may be preloaded, loaded as an intermediate step, or postloaded, and may comprise components such as, but not limited to, an agent to assist in homogeneity, a coagulant agent, an agent to facilitate bonding, an adhesion prevention agent, an antibiotic agent, an anesthetic agent, an anti-inflammatory agent, gelatin (harvested, added in the form of a powder, or in the form of a gelatinous media, any of which can be from the host, synthetic, or from another organism or animal source), or a combination including one or more of the preceding components, or other materials which are capable of for example being introduced into a sterile aspiration syringe and mixed with the patient's own body tissues, cells, or fluids to achieve a suitable or optimal correction of an issue or problem. Any one or more of these components or materials may be preloaded into the system barrel 14 through the luer connection 20, or by removal of the plunger rod 26 and plunger cylinder 24 followed by placement into the system barrel 14. Alternatively or additionally, such components or materials may be loaded into the system barrel 14 after part or all of the desired autologous tissue, cells, or fluid has been withdrawn or otherwise collected into the system barrel 14.

In one example, a blood sample can be withdrawn from a patient and the thrombin and platelets separated one from another using a centrifuge. Either or both of these materials may then be mixed with microparticles (e.g., microspheres) within, for example, the usable volume 19. According to a specific instance wherein thrombin is used from the blood sample, the thrombin can be mixed with microspheres at a ratio of 4:1 by volume of thrombin to microspheres.

Metering to control the usable volume 19 can be implemented based, for example, on maintaining a predetermined ratio by volume of microparticles to biocompatible medium for a given procedure. The mixing ratio of the components of the biocompatible medium (e.g., autologous carrier material) can be chosen according to the needs, and in particular according to the size of the syringe used for the injection. For the application or injection of the microparticles used according to an embodiment of the present invention, the microparticles can be suspended or slurried in a fluid inert medium. In one particular implementation, a ratio of two volume parts of the autologous carrier material and one volume part of the microparticles or polymer microparticles is chosen.

The contents of the system barrel then can be combined (e.g., thoroughly mixed) by using one or more of any number of means, including but not limited to replacing the sterile barrier system closure 12 and placing the metered aspiration, mixing and delivery system 10 in an agitator or shaker apparatus, or attaching the metered aspiration, mixing and delivery system 10 to another sterile syringe and flushing back and forth between the sterile syringes joined by a stopcock, or using other suitable mixing means.

Once the contents of the metered aspiration, mixing, and delivery system 10 have been mixed, a sterile needle or cannula can be attached to the luer end the device, and the contents can be delivered in a desired fashion and/or to a desired location in the patient for repair or augmentation of tissue. To inject the microparticles or polymer microparticles used according to the present invention as an implant in a treatment region, the microparticles can be formed within an autologous carrier material. Degradation or resorption of the autologous carrier material can occur over an appropriate period of time, as outlined in the U.S. Pat. No. 5,344,452. The metered aspiration, mixing, and delivery system 10 can be adjusted to control the amount of material to be delivered, if so desired.

The administering of the tissue treatment implant can be performed on, for example, humans and animals (e.g., horses, dogs, and cats) and can comprises, for example, treating or augmenting tissue, such as, for example, one or more of augmenting a skin defect and/or cosmetically enhancing a facial feature; bulking one or more of a vocal cord, a lower esophageal sphincter, a pyloric sphincter, a bladder sphincter and an anal sphincter; occluding a vascular supply to a tumor; tumor metastasis embolization by way of, for example, blocking a vascular flow exiting a tumor; tumor embolization by intratumor application, blocking a vascular supply to a tumor, blocking a vascular flow exiting the tumor, and/or combinations thereof; a repair or augmentation of a vertebral disk; cartilage augmentation, cartilage repair, and/or combinations thereof; and administration of the tissue implant to one or more of nasal cartilage, ear cartilage, joint cartilage, spinal cord cartilage, and combinations thereof.

Following insertion (e.g., injection) of the biocompatible augmentation or repair material into a region or regions of interest, the biocompatible augmentation or repair material in accordance with one aspect of the present invention may in certain implementations begin to undergo a complete or at least partial biodegradation of, for example, the biocompatible medium (e.g., the autologous carrier material). In accordance with a typical implementation, following insertion of the biocompatible augmentation or repair material, the autologous carrier material is at least partially and, preferably substantially, resorbed into or via tissues of the host mammalian body and/or replaced or supplemented with host tissue (e.g., collagen). In a representative embodiment, the biocompatable medium is both resorbed and replaced with host tissues.

While this invention has been described with respect to various specific examples and embodiments, it is to be understood that the invention is not limited thereto and that it can be variously practiced. Multiple variations and modification to the disclosed embodiments will occur, to the extent not mutually exclusive, to those skilled in the art upon consideration of the foregoing description. Additionally, other combinations, omissions, substitutions and modifications will be apparent to the skilled artisan in view of the disclosure herein. For example, alternate means of harvesting the autologous tissues, cells, or fluids may be employed, and they are not limited to those described above. In addition, the methods of processing (e.g., micronizing) the harvested autologous tissues, cells, or fluids, and the means of mixing the components of the tissue augmentation and/or repair materials can be varied, or the assisting materials that are preloaded into the metered aspiration, mixing, and delivery system can be reduced or expanded to exclude or include any number of additives or chemical or biological agents. Accordingly, the present invention should not be limited by the disclosed embodiments, but is to be defined by reference to the appended claims.

What is claimed is:

1. A tissue treatment implant for administration to a patient, comprising:
    a bulking agent consisting of a plurality of round and smooth polymethylmethacrylate microparticles preloaded within a mixing and delivery system; and
    an autologous carrier made from cells obtained from soft tissue withdrawn from said patient into the mixing and delivery system;
    wherein the bulking agent and the autologous carrier are combined within the mixing and delivery system and then delivered to the treatment location.

2. The tissue treatment implant of claim 1, wherein the autologous carrier contacts at least a portion of the plurality of round and smooth polymethylmethacrylate microparticles.

3. The tissue treatment implant of claim 1, wherein the autologous carrier contacts substantially all of the plurality of round and smooth polymethylmethacrylate microparticles.

4. The tissue treatment implant of claim 1, wherein the autologous carrier is mixed with the plurality of microparticles.

5. The tissue treatment implant of claim 1, wherein the autologous carrier comprises bodily tissue withdrawn from the patient's connective tissue.

6. The tissue treatment implant as set forth in claim 1, wherein the autologous carrier comprises one or more of adipose tissue, a component of adipose tissue, and combinations thereof.

7. The tissue treatment implant as set forth in claim 6, wherein the adipose tissue is derived from one or more of subcutaneous fat, loose or flaccid body fat, and combinations thereof.

8. The tissue treatment implant as set forth in claim 1, wherein the adipose tissue is derived from one or more of fat around the patient's waistline, a component of the fat, and combinations thereof.

9. The tissue treatment implant as set forth in claim 1, wherein the autologous carrier comprises one or more of marrow, a component of marrow, and combinations thereof.

10. The tissue treatment implant as set forth in claim 1, wherein the autologous carrier comprises one or more of fibrous tissue, a component of fibrous tissue, and combinations thereof.

11. The tissue treatment implant as set forth in claim 1, wherein the autologous carrier comprises one or more of muscle tissue, a component of muscle tissue, and combinations thereof.

12. The tissue treatment implant as set forth in claim 1, wherein the autologous carrier comprises one or more of cartilage tissue, a component of cartilage tissue, and combinations thereof.

13. The tissue treatment implant as set forth in claim 12, wherein the cartilage tissue is derived from one or more of ear tissue, ribs tissue, and knee tissue.

14. The tissue treatment implant as set forth in claim 1, wherein the autologous carrier comprises cells of dermal tissue.

15. The tissue treatment implant as set forth in claim 1, wherein the autologous carrier comprises cells of mucosa.

16. The tissue treatment implant as set forth in claim 1, wherein the autologous carrier comprises one or more of cells of the patient in any ration, a component of the cells, and combinations thereof.

17. The tissue treatment implant as set forth in claim 1, wherein the autologous carrier comprises one or more of stem cells of the patient in any ration, a component of the stem cells, and combinations thereof.

18. The tissue treatment implant as set forth in claim 1, wherein the autologous carrier comprises cells of one or more of (a) connective tissue, (b) adipose tissue, (c) marrow, (d) fibrous tissue, (e) muscle tissue, (f) cartilage tissue, (g) dermal tissue, (h) mucosa, and (i) combinations thereof.

19. The tissue treatment implant as set forth in claim 1, wherein:
the microparticles possess one or more of (a) sizes between about 10 microns and about 500 microns, (b) smooth surfaces free from corners, edges, peaks and projections, (c) at least one of elliptical, cylindrical, and spherical forms, and (d) one or more of smoothed or rounded corners, edges, peaks, and projections; and
the microparticles comprise one or more of a porous surface, a porous body, a shell-like structure, a hollow interior, a metallic coating, a carbon coating, a carbon nanotube coating, components thereof, and combinations thereof in any ratio.

20. The tissue treatment implant as set forth in claim 1, wherein the microparticles have a short-term effectiveness of up to about 6 months, and comprise one or more of collagen; hyaluronic acid; and genetically altered cells, tissues or microorganisms.

21. The tissue treatment implant as set forth in claim 1, wherein the microparticles have a medium-term effectiveness of up to about 3 years, and comprise one or more of collagen; hyaluronic acid; and genetically altered cells, tissues or microorganisms.

22. The tissue treatment implant as set forth in claim 1, wherein the microparticles have a long-term effectiveness of more than about 3 years, and comprise any type of collagen, hyaluronic acid; and genetically altered cells, tissues or microorganisms.

23. The tissue treatment implant as set forth in claim 1, wherein the microparticles comprise one or more of polylactic acid, a ceramic material, polymethacrylate, polymethylmethacrylate (PMMA), polypropylene, or polytetrafluoroethylene (PTFE).

24. The tissue treatment implant as set forth in claim 1, wherein the microparticles have a long-term effectiveness of more than about 3 years, and comprise purified cytoskeleton of unicellular or multicellular algae.

25. The tissue treatment implant as set forth in claim 1, wherein the microparticles comprise two or more of collagen, hyaluronic acid, polylactic acid, ceramic materials, polymethacrylate, polymethylmethacrylate (PMMA), polypropylene, polytetrafluoroethylene (PTFE), and purified algae cytoskeleton.

26. The tissue treatment implant of claim 1, wherein the round and smooth polymethylmethacrylate microparticles are sterile.

27. The tissue treatment implant of claim 1, further comprising one or more of sterile water, an aqueous isotonic solution of saline, an aqueous isotonic solution of phosphate salts, a hypertonic aqueous solution, a hypotonic solution, a component thereof, and combinations thereof.

28. The tissue treatment implant of claim 1, further comprising a sterile aqueous thickening agent.

29. The tissue treatment implant of claim 28, wherein the sterile aqueous thickening agent comprises one or more of collagen, gelatin, hyaluronic acid, methyl-cellulose, polylactic acid, a component thereof, and combinations thereof.

30. The tissue treatment implant of claim 1, wherein the tissue treatment implant is disposed within an aspiration syringe.

31. The tissue treatment implant of claim 1, wherein the tissue treatment implant is disposed within a metered aspiration, mixing and delivery system.

32. The tissue treatment implant of claim 31, wherein the metered aspiration, mixing and delivery system comprises a rotatable metering sleeve.

33. The tissue treatment implant of claim 31, wherein the metered aspiration, mixing and delivery system further comprises a micronizing device.

34. The tissue treatment implant of claim 33, wherein the micronizing device comprises one or more of structure configured to perform physical micronization, structure configured to perform ultrasonic micronization, a component of either, and combinations thereof.

35. The tissue treatment implant of claim 1, further comprising an agent to assist in homogeneity.

36. The tissue treatment implant of claim 1, further comprising a coagulant agent.

37. The tissue treatment implant of claim 1, further comprising an agent to facilitate bonding.

38. The tissue treatment implant of claim 1, further comprising an adhesion prevention agent.

39. The tissue treatment implant of claim 1, further comprising an antibiotic agent.

40. The tissue treatment implant of claim 1, further comprising an anesthetic agent.

41. The tissue treatment implant of claim 1, wherein the microparticles have a long-term effectiveness of more than about 3 years.

\* \* \* \* \*